(12) United States Patent
Patrickson et al.

(10) Patent No.: US 9,886,873 B2
(45) Date of Patent: Feb. 6, 2018

(54) METHOD AND APPARATUS FOR DEVELOPING MEDICAL TRAINING SCENARIOS

(75) Inventors: Clive William Patrickson, Stavanger (NO); Lars Kirkeskov Sorup, Stavanger (NO); Martin Hetland, Stavanger (NO)

(73) Assignee: Laerdal Medical AS, Stavanger (NO)

( * ) Notice: Subject to any disclaimer, the term of this patent is extended or adjusted under 35 U.S.C. 154(b) by 0 days.

(21) Appl. No.: 13/451,052

(22) Filed: Apr. 19, 2012

(65) Prior Publication Data
US 2013/0280685 A1 Oct. 24, 2013

(51) Int. Cl.
G09B 23/28 (2006.01)
G09B 9/00 (2006.01)
G09B 23/30 (2006.01)
G06F 19/00 (2011.01)

(52) U.S. Cl.
CPC ........... *G09B 23/28* (2013.01); *G09B 9/00* (2013.01); *G09B 23/30* (2013.01); *G06F 19/3437* (2013.01); *G06F 19/3481* (2013.01)

(58) Field of Classification Search
CPC .......... G09B 23/28; G09B 23/30; G09B 9/00; G06F 19/3437; G06F 19/3481
USPC .......... 434/219, 323, 365, 403, 429
See application file for complete search history.

(56) References Cited

U.S. PATENT DOCUMENTS

| | | | |
|---|---|---|---|
| 6,193,519 B1 | 2/2001 | Eggert et al. | |
| 6,739,877 B2 | 5/2004 | Arington et al. | |
| 6,918,771 B2 | 7/2005 | Arington et al. | |
| 7,805,381 B2 | 9/2010 | Habichler et al. | |
| 7,997,904 B2 | 8/2011 | Deering | |
| 2003/0187362 A1* | 10/2003 | Murphy | G06T 7/0012 600/508 |
| 2004/0046792 A1* | 3/2004 | Coste et al. | 345/763 |
| 2004/0175684 A1* | 9/2004 | Kaasa et al. | 434/262 |
| 2005/0123892 A1 | 6/2005 | Cornelius | |
| 2005/0181342 A1* | 8/2005 | Toly | 434/262 |
| 2005/0186549 A1 | 8/2005 | Huang | |
| 2005/0187461 A1* | 8/2005 | Murphy et al. | 600/416 |
| 2007/0202475 A1 | 8/2007 | Habichler et al. | |
| 2007/0203711 A1 | 8/2007 | Nation et al. | |
| 2007/0208572 A1 | 9/2007 | Habichler et al. | |
| 2008/0171311 A1 | 7/2008 | Centen et al. | |
| 2008/0312565 A1 | 12/2008 | Celik-Butler et al. | |
| 2010/0035225 A1 | 2/2010 | Kerfoot, III | |

(Continued)

OTHER PUBLICATIONS

Jensen et al., "Using e-learning for maintenance of ALS competence", 2009, Elsevier Ireland Ltd., pp. 903-908.

(Continued)

*Primary Examiner* — Jack Yip
(74) *Attorney, Agent, or Firm* — 24IP Law Group; Timothy R DeWitt

(57) ABSTRACT

A medical training development system for development of medical training scenarios (15) is disclosed. The medical training development system comprises a repository (110) with a plurality of pre-programmed event modules (120) and pre-programmed medical training scenarios (15'). A scenario programming system (140) is connectable to the repository (110) for accessing the event modules (120) and the pre-programmed medical training scenarios (15) for programming the medical training scenarios (15').

4 Claims, 3 Drawing Sheets

(56) References Cited

U.S. PATENT DOCUMENTS

| | | |
|---|---|---|
| 2010/0227303 A1 | 9/2010 | Deering |
| 2010/0305928 A1 | 12/2010 | Cohen |
| 2011/0165542 A1* | 7/2011 | Campbell et al. ............ 434/219 |
| 2011/0223573 A1 | 9/2011 | Miller |

OTHER PUBLICATIONS

Laerdal, "Heartcode PowerPoint presentation", May 20, 2010.
M. H. Oermann et al., "HeartCode(TM) BLS with Voice Assisted Manikin for Teaching Nursing Students: Preliminary Results", Teaching With TechnologylBasic Life Support, vol. 31 No. 5, 2010, pp. 303-308.
B-Line Medical, "SimCapture—Record. Review. Results.", 2011, www.blinemedical.com, American Heart Association! American Stroke Association "Learn and Live", PowerPoint.
Seethala et al., Abstract"Approaches to improving cardiac arrest resuscitation performance" (abstract), Jun. 2010 Lippincott Williams & Wilkins, Inc.
de Vries et al., Abstracts "Self-training in the use of automated external defibrillators: The same results for less money" (abstract), Jan. 2008.
Laerdal, "Product Information Bulletin—11-002 SimCenter", Apr. 19, 2011.
Laerdal, HealthStream "Sim Ventures" Announcement, Jun. 23, 2010.
HealthStream, Press release "HealthStream Acquires 50% Stake in Laerdal Medical's Advanced Video System, a Simulation Debriefing System", 2011.
J. Barris, "Healthcare Simulation and Its Potential Areas and Future Trends", SES M's magazine 2011/No. 1 (January) pp. 1-6 (2011).

* cited by examiner

METHOD AND APPARATUS FOR DEVELOPING MEDICAL TRAINING SCENARIOS

CROSS-REFERENCE TO RELATED APPLICATIONS

None.

FIELD OF THE INVENTION

The field of the invention relates to a medical training development system and a method for developing a medical training scenarios as well as a computer program product stored in a non-volatile memory and which, when executed on a general-purpose computer, enables the general-purpose computer to perform the method.

BACKGROUND OF THE INVENTION

Medical training systems are known in the prior art. One example of a medical training system is a medical simulation system, such as those produced by the Laerdal Medical AS based in Stavanger, Norway. Such medical simulation systems enable the training of students in responding to the medical needs of patients by simulating a medical emergency or other medical procedure. These medical needs include, but are not limited to, casualty assessment, emergency response, birthing, and cardiopulmonary resuscitation (CPR). Cardiopulmonary resuscitation is an emergency procedure that is performed in an effort to manually preserve intact brain function, until further measures can be taken to restore normal blood circulation and breathing to a patient.

The medical simulation systems often use manikins. The manikin is a life-sized anatomical human model used as a teaching aid in medical education for training students, for example doctors, nurses, paramedics, as well as other learners in, for example, emergency care and resuscitation of humans. A number of companies produce manikins. For example, Laerdal have produced manikins in various forms since the 1960s. Generally, manikins are three-dimensional models of all or part of a human being and are intended to be as realistic as possible in order to provide the learners with a realistic situation. The manikin can be used to instruct learners using a so-called "training scenario". The training scenarios are designed to be realistic simulations of medical emergencies that might occur in real-life. An instructor can institute one or more of the training scenarios and view how the learner responds to the implemented training scenario.

More recently e-learning systems for training scenarios have been introduced. For example, the Laerdal Medical has developed a self-directed, computer-based course for obtaining basic life support certification and is marketed under the trade name HeartCode™. The HeartCode system enables students to obtain certification and includes a local database recording the names of the students who achieve certification.

A number of e-learning systems for medical simulation are known. For example, Laerdal Medical offers a SimStore centre together with the US Company HealthStream, Nashville, Tenn., which is an e-warehouse that supports the distribution and sale of medical simulation content. Further details of the SimStore and related SimCenter product are included in the Laerdal product information bulletin 11-002, dated 18 Apr. 2011. This product information bulletin describes the global launch of the SimCenter product. The medical simulation content in the SimStore is used with training products and other medical simulation products, such as those produced by Laerdal Medical.

A number of patent applications disclose integrating various e-learning systems. For example, U.S. Pat. No. 6,193,519 (Eggert et al, assigned to Gaumard Scientific) teaches an interactive, computerised education system that includes an interactive program to use with a simulator, such as manikin, and virtual instruments for performing simulated patient care activity under the direction of a computer program. The interactive program displays a selection of modules to assist a student in learning patient care protocols. The modules are selectable by the student for providing different interactive training sessions involving the different patient care protocols. The virtual instruments used with the simulator in performing the patient care activity co-operate with sensors in the manikin but interface with the computer program and thus provide feedback to the program regarding activity of a student, and confirm proper placement and use of the virtual instruments on the simulator.

Similarly, U.S. Patent Application Publication No. 2005/0186549 (Huang) teaches a method and skills assessment tool for managing a testing session in a clinical skills testing centre that comprises a plurality of assessment stations. The method disclosed includes configuring a plurality of the assessment stations by associating each of the assessment stations with a case type prior to the beginning of the testing session, receiving electronic identification of a student at one of the assessment stations and, in response to receiving the student's identification, automatically assigning the student to one of the assessment stations.

U.S. Patent Application Publication No. 2011/0223573 (Miller et al. assigned to Kb Port) teaches a method and apparatus for multiple medical simulator integration. The apparatus provides multiple medical simulators, which simultaneously receive at least one electronic data source input from each medical simulator, and puts these electronic data source inputs into a common digital memory buffer in a time-stamped manner for at least a given training event. Each one of the electronic data source inputs forms a data record throughout the event of a simulated parameter of the training simulator or a physical parameter of the training simulator. The common memory buffer allows independent, simultaneous, synchronised, user-controlled playback of the individual input received within the memory buffer in any number of user-defined configurations.

An article "Healthcare Simulation and Its Potential Areas and Future Trends", SES M's magazine 2011/No. 1 (January) pages 1-6 by J. Barris discusses the pressure of controlling costs in the health care services and reports on healthcare simulation as well as identifying the most relevant topics for future research. The article notes that healthcare simulation has a broad application potential for clinical simulation, operational simulation, managerial simulation and educational simulation. One of the issues associated with healthcare simulation is the growing complexity of healthcare processes. This complexity is also reflected in the growing complexity of the medical simulation tools. For example, it is necessary to create data from many different medical and other healthcare simulations and to compare this data. The data needs to be compared across students, institutions (such as hospitals or universities) and private clinics. The data therefore needs to be developed in a common format that allows such comparisons to be made.

The increasing complexity of the healthcare protocols means that the medical simulations have become more complex. There are, however, common elements or common events in the medical simulations that can be reused and reprogrammed in different medical simulations. The performance of such common events can also be compared against the performance by other students of the common events and against the performance of the same student in a different context using the same common event.

The term "student", as used in this disclosure, is not intended to exclusively mean an undergraduate or college student who is attending an MD course, a B. Med. course or similar. The term "student" is also intended to apply to health-care professionals, such as an already-qualified nurse, doctor or paramedic who requires basic and refresher training to maintain his or her competence. It will be appreciated that the term "student" is therefore widely understood in the context of this disclosure to mean those people undergo training using medical simulation devices, e-learning or practical experience.

In addition to a traditional medical simulation system, new types of medical training systems and medical monitoring systems have been introduced in order to monitor and evaluate students in real-life situations. For example, U.S. Patent Application Publication No. 2008/0312565 (assigned to the Board of Regents of the University of Texas system, Austin, Tex. and Laerdal Medical, Stavanger, Norway) describes a CPR sensor in the form of a card. The CPR sensor includes a thin and substantially flat flexible substrate having one or more sensor arrays, a power source, an output interface, a processor or analogue circuit incorporated into a credit-card flat flexible substrate. The CPR sensor of the US '565 publication can be easily carried in a wallet or other personal belonging or item of clothing so that the CPR sensor can be located quickly during an emergency. The CPR sensor is placed on or near to the hands of the person administering CPR and is able to provide immediate feedback to the person administering CPR to indicate that he or she is correctly administering CPR. The incorporation of the output interface enables a transfer of the real-life data to a database for further evaluation at a later stage. The storage of the real-life data in the database can be invaluable when reviewing the person's competence in performing CPR and/or for evaluating the performance of the CPR in the event that there is an enquiry or a lawsuit related to the performance of the CPR.

SUMMARY OF THE INVENTION

A medical training development system for development of medical training scenarios is disclosed in this document. The medical training system comprises repository with a plurality of pre-programmed event modules and/or pre-programmed medical training modules, a scenario programming system connectable to the repository and which can be used to access the pre-programmed event modules and pre-programmed medical training modules in the repository for programming the medical training scenarios and for passage to a central administrative module.

The medical training development system may also include a further medical training scenario database from in which the previously programmed and newly developed medical training scenarios are stored and later accessed to run on a training device, for example a manikin, a general-purpose computer, a tablet computer, a smartphone or a personal computer. The use of the pre-programmed event modules to build up the medical training scenarios enables a consistency of coding as well as cross-correlation of data across more than one of the medical training scenarios. Further development of existing pre-programmed medical training modules enables the addition of new or modified features whilst retaining existing coding. This is efficient as less new coding needs to be developed, and data previously generated can be directly compared with data generated by running the newly developed medical training modules.

In one aspect of the invention, the pre-programmed event modules and/or the pre-programmed medical training modules are in the form of XML files, which can be interpreted by the general-purpose computer, tablet computer, smartphone, personal computer or the manikin. It will be appreciated that this does not exclude other types of data formats or coding languages from being used.

The disclosure also discloses provision of a student record database having a plurality of records that relate to the learning experience of the students. The data in the records is generated from the instructions in the medical training event modules or from data supplied and entered by an instructor.

A method for developing a medical training scenario is also disclosed. The method comprises selecting one or more from the plurality of the pre-programmed event modules and/or the pre-programmed medical training modules and combining the selected ones to produce a medical training module for running on a medical training device. In one aspect of the invention, common data elements are programmed using, for example XML tags, for use across at least two of the pre-programmed event modules or the pre-programmed medical training modules. These common data elements enable a comparison of the student's performance in performing different ones of the medical training scenarios implemented by the medical training modules.

A data store having a plurality of non-transitory memory elements for storing coding relating to a plurality of the pre-programmed event modules and/or the medical training modules is also disclosed. Finally, a computer programmed product stored on a non-volatile medium and having a first logic for accessing the repository to select one or more of the pre-programmed event modules and/or the pre-programmed medical training modules, second logic for combining the selected ones of the pre-programmed event modules and/or the pre-programmed medical training modules to generate the medical training scenario, and third logic for passing the medical training scenario to run on a training device is disclosed.

DETAILED DESCRIPTION OF THE INVENTION

The invention will now be described based on the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Figure 1:
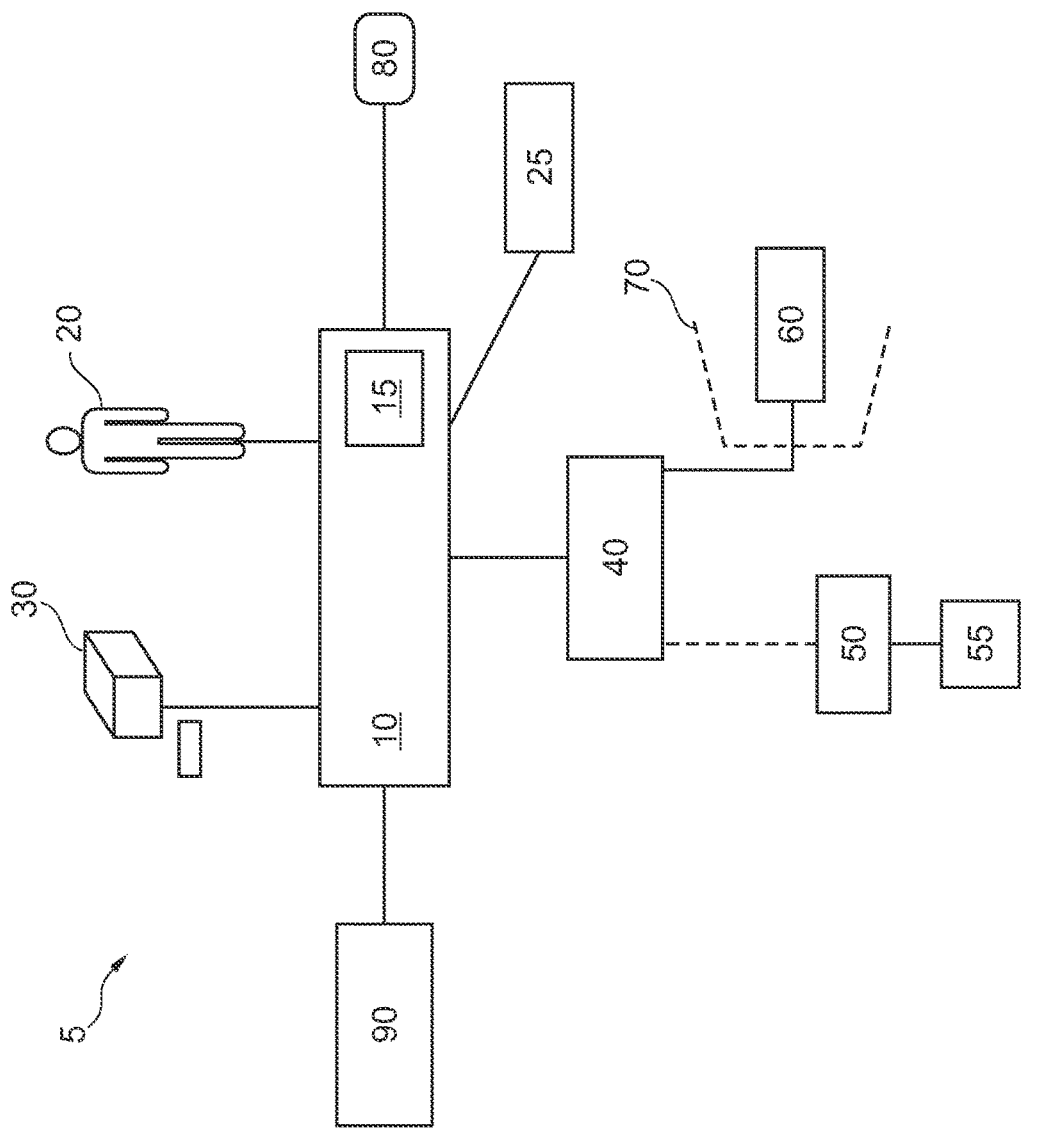
FIG. 1 shows an overview of the medical training system.

A medical training development system 5 is shown in an architecture view in FIG. 1. The medical training system 5 has a central administrative module 10 that is running on a general-purpose computer, such as a server. It will be appreciated that the central administrative module 10 may be run as a local sever or a remote server or be part of a module running on a cloud server. The central administrative module 10 includes one or more medical training modules 15 that may be stored on the same general-purpose computer or in a separate data store.

The medical training modules 15 include, but are not limited to training scenarios with simulations of medical procedures, such as cardio pulmonary resuscitation (CPR) or other advanced life support cases. It will be appreciated that many such medical training modules 15 are possible and that variations of the medical training modules 15 are possible. For example, one of the medical training modules 15 may implement medical training scenarios relevant to an adult but a similar medical procedure performed on an infant requires a different or adapted medical training module 15 because of a modified medical training scenario. A data entry device 25 is used by an instructor to enter data and/or control the medical training scenario.

The medical training modules 15 are programmed to run a patient simulator, such as a manikin 20 or a personal computer 30 or in a central administrative module 10 accessed by a remote workstation. The personal computer 30 can be a stand-alone personal computer, a dumb terminal, a tablet computer or a smartphone.

It is known that the different medical training modules 15 running on the central administrative module 10 have a degree of commonality in which similar medical skills are trained. At least some of these medical skills are independent of the type of medical procedure trained by one of the medical training modules 15. These similar medical skills represent examples of "events". The term "event" is used in this context to indicate various components or stages of the medical procedure or training scenario. The common events may have common data elements associated with them. The common data elements are, for example, parameters indicative of a student's performance in performing one or more of the medical skills across different ones of the medical training modules 15. There are also likely to be "specific" events which are specific to the medical training scenario being performed and have nothing to do with any other one of the medical training scenarios.

A medical simulation generally comprises a plurality of events. The events and the order of the events will change over the course of the medical training scenario. For example, a first series of events might occupy the first ten minutes of the medical training scenario undertaken by the student. After running the medical training module 15 for ten minutes, the medical state of a patient might be deemed to change dramatically. This change in the medical state can be done automatically (i.e. is pre-programmed into the medical training scenario) or could be done by an instructor monitoring the student's performance and manually initiating the change. The medical training scenario would then change from the first series of events to a second series of events. The manner in which the instructor uses the data entry device 25 to change the running order of the set of events or introduces new events is outlined below.

An event category is a grouping of events. Each one of the events will be assigned a default category, but the category can generally be changed, or a new category defined. The type of category associated with the event is assigned to the event and stored with the event in metadata. Similarly, a composite event is a small group of individual events that are logically located or grouped to each other. For example, the so-called "six rights of medication" comprise six different events. Each one of the six different events is separately programmed (and can be called up independently). The different events representing each one of the six rights are thus available individually, but are also available as a composite event.

A manikin device 20 is also connected to the central administrative module 10. The connection between the manikin 20 and the central administrative module 10 can be by cable and/or wireless, but this is not limiting of the invention.

The personal computer or other form of display terminal 30 is connected to the central administrative module 10 by cable and/or wireless. A student and/or an instructor can operate the personal computer 30. The personal computer 30 enables access to the medical training modules 15 running on the central administrative module 10 and may enable access to patient records in a patient record database 60, if the student or instructor has sufficient access rights to enable access to this private data. It will, however, be appreciated that laws governing access to such private data are extremely restrictive and thus the training modules 15 may write data to such patient records database 60, but rarely allow access to real patient records. The patient records database 60 may be protected by a firewall 70. It may be possible to allow access anonymously or to dummy patient records. In many training system no patient records in the patient records database 60 or only dummy patient records are present.

A data manager 40 is connected to central administrative module 10 by cable or wireless. The function of the data manager 40 is to extract from the central administrative module 10 any data relevant to the performance of the student in carrying out the medical training scenario. The data is extracted, in one aspect of the system, in a form of a long file. The data manager 40 can receive data from and pass data to the manikin 20 and/or from the personal computer 30 and/or from an instructor entering data on the data entry device 25. The data manager 40 can receive the data from or pass the data to the patient records database 60 (as disclosed above) and/or receive or write the data into a student records database 50. The data manager 40 is shown as a separate unit in this figure, but can also be incorporated into the central administrative module 10 or elsewhere.

The data manager 40 can be part of a learning management system which enables the student to monitor his or her learning goals and outcomes.

The data in the student records database 50 includes the names of the student, e.g. as entered through the personal computer 30, and also any data relating to the types of medical competences for which the student is trained as well as expiry dates of any certification requirements for a particular medical competence. The student records database 50 also includes verifiable keys accessable by, for example, an employer or regulatory agency to verify any information and certify that the information stored in the student records database 50 is genuine.

Figure 2:
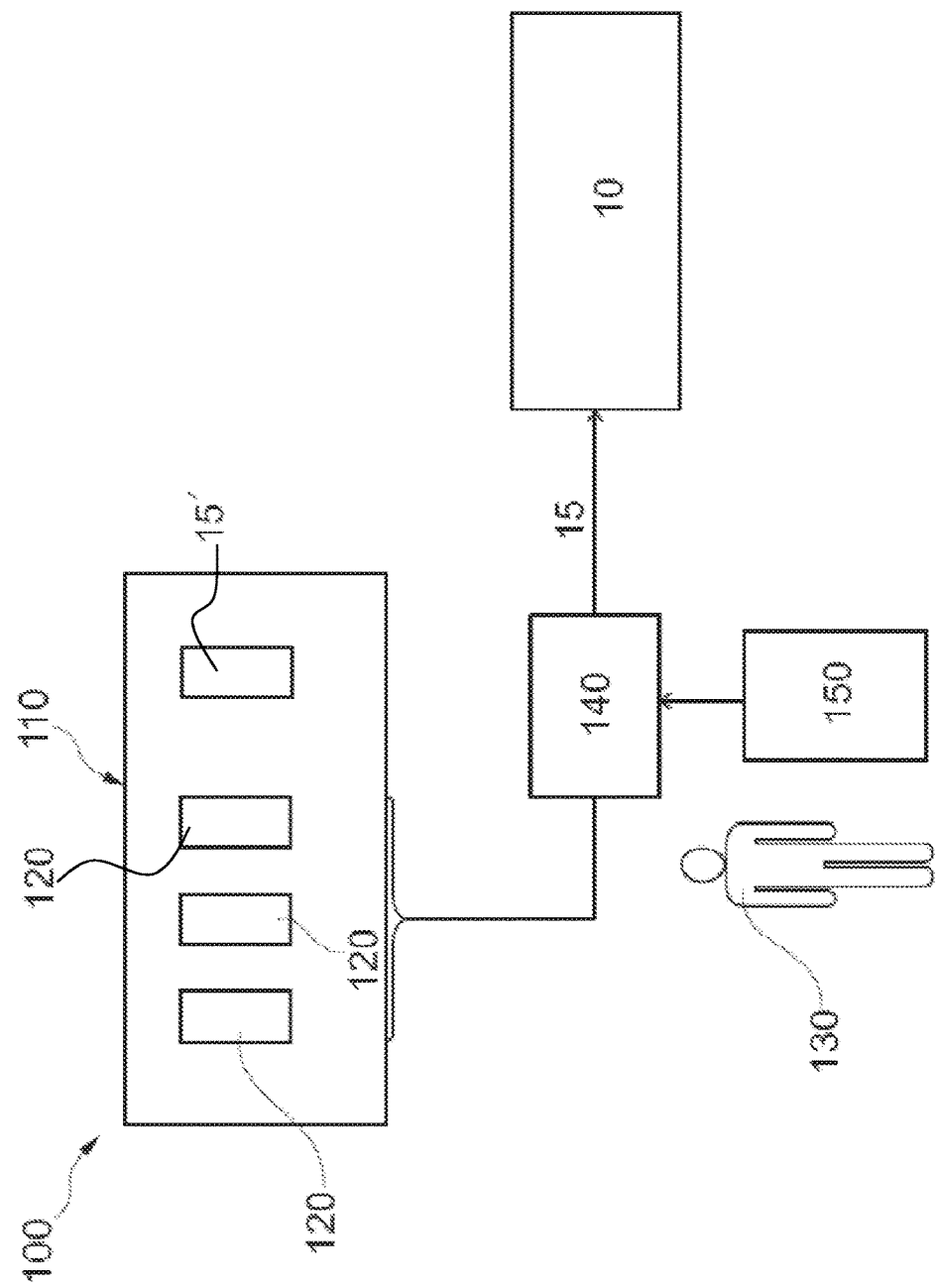
FIG. 2 shows a flow diagram of the method for training students in medical matters.

FIG. 2 shows an example of a medical training scenario development system 100. The medical training scenario development system 100 is used to create and/or amend the medical training modules 15 for running on the central administrative module 10, one or more manikin devices 20 and/or one or more of the personal computers 30, as explained above.

The scenario development system 100 comprises a repository 110 and a scenario programming system 140. The scenario programming system 140 is programmed by a scenario programmer 130. The repository 110 comprises a plurality of event modules 120 and may also comprise pre-programmed medical training modules 15'. The scenario development system 100 is shown in this figure as a separate unit, but it will be understood that the scenario development system 100 could also be part of the central administrative module 10 or run on the personal computer 30.

The event modules 120 comprise a series of instructions (coding) that can be used to operate the manikin devices 20, the central administrative module 10 and/or the personal computer 30 to implement the events. The event modules 120 will include instructions to extract any required data from the student records database 50 and from the personal computer 30 or manikin devices 20 as well as instructions to write the data into the student records database 50 (or other database). The event modules 120 are pre-programmed and can be used in the development of multiple medical training scenarios.

The scenario development system 100 may also include one or more of the existing (i.e. pre-programmed) medical training modules 15' and can be used to change, update, or recode the existing ones of the medical training modules 15. In other words a "mother" one of the medical training modules 15' can be used to generate a "daughter" one of the medical training modules 15''.

In one aspect, the event modules 120 (and the medical training modules 15, 15',15'') are programmed using an XML schema. The XML schema is stored in a non-volatile memory which forms the repository 110. The non-volatile memory contains a plurality of memory elements for physical storage of data. The XML schema includes the instructions for the operation of the central administrative system, the manikin devices 120 and the personal computers 30, as well as metadata.

The metadata is "data about data" and is, in essence, descriptors which describe, for example, the roles of the students and/or the instructors, the intended outcomes of the medical training scenario, parameters collected about the performance of the student. The metadata can be interpreted by the manikin 20, the data entry device 25, the personal computer 30, the data manager 40, etc., and used partially identify the events programmed by the event module 120 and to arrange for the collection of data which is relevant to the performance by the student of the event. The use of the metadata enables the cross-reference of the collected data across one or more of the events.

Examples of the metadata include the following:
ViewItems Key—the unique ID of an event
DisplayName Lang—the language of the event, for translation purposes
ViewItem—an event
Event—a normal event, no extra values
StringEvent—an event that has a text-based value
EnumEvent—an event that has multiple text-based values
IntEvent—event that has an integer value
DoubleEvent—an event that has a numerical value
DrugEvent—an event with values for dose and route
CompositeViewItem—and event with sub-events within it
BoolEvent—An event that has a true/false value
EnumEvent DefaultValue—the default value of an event of type enumevent
AllowMultiple—determines whether or not you can register multiple values for the event or not
Id—the name of the event
Lang—the language of the event
Roles—if the event have a role or many roles associated with it, meaning e.g. Head nurse are expected to carry out this event
Role Lang—name of the role
InstructorProperties—properties that deals with creating a more intelligent workflow during simulation
Critical—shows an icon on events that might lead to drastic consequences in the scenario
ShowCounter—whether or not the event should show a counter for every time it is registered
Count—the actual number of times the event has been registered (requires enablement of the ShowCounter
Highlight—the next event anticipated according to the scoring algorithm should be highlighted so that it is easier to find for the instructor
ShowOnceInView—if this is set to true, the event will disappear from the view on an instructor's device once the event has been registered. Handy for events that only happens once
HideWhenTimeInView_Seconds—maybe an event is only relevant for the first 5 minutes, after that the event probably will not occur at all. This is the ability to auto-hide the event after a given time.
EventInfo—this is information about the event, e.g. the definition of what the event actually is.
LogMessage Lang—This is information that goes into the log together with the registration of the event.
UnsetEvent ShowMainEvent—some events have an "anti-event" connected to them, such as intubate vs extubate
Id—the name of the anti-event
Lang—language for the for translations purposes
AntiRoles—roles for the anti-event
EnumValue—the actual value of the event, which it is set to upon registration The scenario programmer 130 uses the event modules 120 and/or the pre-programmed medical stored in the event modules database 110 to develop his or her own medical training modules 15'. So, for example, the scenario programmer 130 can always use the event modules 120 relating to "washing of hands" in various different medical training scenarios. The metadata associated with the event module 120 "washing of hands" will enable a comparison to be made across different medical training scenarios to see whether individual ones of the students consistently wash their hands and whether the same student consistently washes his or her hands when performing different ones of the medical training scenarios. This information can be stored in the common data elements as part of the student records database 50. The event modules 120 with their standardised reports embedded in the XML code can be used to send the data to the student record database 50, as noted above.

The use of the event modules 120 also ensures consistency of coding. There will not be slight variations between events that should be otherwise identical. The event modules 120 therefore enable a greater consistency of training, an increased productivity of the development of the medical training modules 15 by the scenario programme 130 who does not need to consistently reprogram simple tasks and a greater degree of comparison across various ones of the medical training modules 15 and the student's performance.

It will be appreciated that the event modules database 110 comprises not only event modules 120, but can also comprise composite events which have been pre-programmed (such as the afore-mentioned six rights of medication). It will be furthermore appreciated that the scenario programmer 130 can additionally program his or her own additional code 150 in the scenario programming system 140 if no pre-programmed event modules 120 are available. This additional code 150 can be then stored and re-used by another scenario programmer if the additional code 150 is stored in the depository 110 or elsewhere.

The output of the scenario programming system 140 is the medical training module 15 or updated medical training module, which is provided across to the central administrative module 10.

The patient records database 60 is one of the most sensitive databases and is generally accessed only when a medical procedure is performed on a real-life patient as opposed to a performance of the medical training scenario on the manikin 20 (or on the personal componter 30) and the data relating to the performance of the student on the real-life patient is incorporated into the central administrative module 10.

A quality control system 90 is connected to the central administrative module 10 for monitoring the quality of the training. The quality control 90 will generally have access to anonymous data from the central administrative module 10, i. e. without access to the student's names or other identification and/or the patient's names and/or other identifications. The quality control system 90 can also be used to data mine the student record database 50 in order to compare the quality of the training across the students. The use of the metadata in the event modules enables the student record database 50 to be populated with standardised data allowing such comparisons to be made.

It will be appreciated that the manikin 20 shown here does not need to be placed in a central training unit. On the contrary, in order to ensure that students are regularly trained the manikin 20 can be housed in a side room near a ward of a hospital. This will allow the student to undertake regular medical training whenever it becomes convenient for him or her. There is no need for the student to register for a training course in order to obtain recertification.

The advantage of having the manikin 20 near the student's work place is also that the student can be instructed, for example by email, to undertake regular refresh courses in order to maintain his/her competence in the performance of medical procedures. The refresher courses are one example of the medical training modules 15 and different refresher courses can be given at different intervals.

The personal computer 30 will also enable the student to undertake regular and continuous education on various aspects of medical procedure. For example, the guidelines of the American Heart Association on CPR have recently been updated. The central administrative module 10 can inform the student about the update and arrange for the student to take an appropriate one of the medical training modules 15 in order to be updated on the revised medical procedure. The central administrative module 10 can record the student's completion of the training and provide feedback to the student and/or the quality control 90 to enable important action to be taken.

It will be appreciated that the use of the event modules 120 easily allows variations of training to be carried out so, for example, the medical training scenario can be slightly altered between different refresher causes for the individual students to ensure that the students are performing well, even when confronted with new variations on the medical training scenario. The metadata in the event modules 120 allows an easy comparison between the student's performance on the current medical training scenario with the student's past performance.

The manikin 20 and/or the personal computer 30 record the student's performance when performing the medical training module 15 and provide feedback to the central administrative module 10. In particular, this feedback can include whether the student requires further training and/or has meet the requirements to obtain certification.

In one further aspect of the invention, an instructor or an invalidator has a data entry device 25 that he or she uses to record the student's performance and to pass details of the performance to the central administrative module for review and recording.

The data entry device 25 receives instructions and information that have been encoded into the medical training module 15. The use of the XML data means that similar functions can be performed by different ones of the data entry devices 25, if these data entry devices 25 are capable of doing these functions. The data entry device 25 includes the code which interprets the XML data. The data entry device 25 also receives instructions to enable the instructor to change the sequence of the medical training scenario.

It will be appreciated that the functions of the central administrative module 10, the quality control 30 and the data manger 40 overlap to a certain extent. These are generally implemented as computer programs running on a general-purpose computer and the instructions are stored on a non-volatile memory device. It will be further appreciated that the components may be implemented in different manner, depending on the general-purpose computer system on which they are running In one further aspect of the invention the data entry device 25 may be a code sheet completed by a nurse or instructor and logged in an appropriate log. Any data from the log or code sheet can be transferred either electronically or by manual entry to the central administrative module 10.

One further example of the data entry device 25 used in this disclosure is the advanced video system developed by Laerdal and described in a press release, dated 30 Mar. 2011. The advanced video system will interpret the XML files supplied with the medical module 15 and arising from the pre-programmed event module in order to understand which items should be videoed and the manner in which the items should be stored in the student record database 30.

Figure 3:
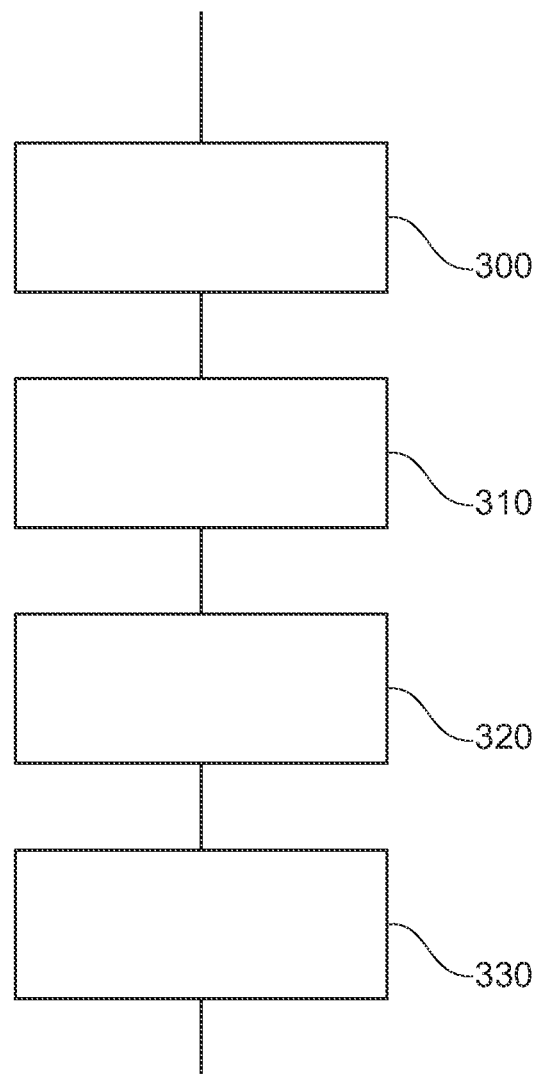
FIG. 3 shows a flow diagram of the method for collating student performance data from a real-life medical procedure.

FIG. 3 shows an example of a workflow used in developing the medical training scenario 15. In a first step 300 the scenario programmer 130 establishes the purpose of the medial training scenario to be implemented by the medical training module 15 to be developed and sketches out the events required in the medical training module 15. In the following step 310, the scenario programmer 130 chooses those event modules 120, composite events or pre-programmed medical training modules 15' which are appropriate to the (new) medical training module 15 or 15" that he or she is developing. It will be appreciated that the scenario programmer 130 should attempt to re-use as many ones of the event modules 120 possible.

In a further step 320, the scenario programmer 130 codes in the scenario programming system 140 those additional lines of code necessary to "glue" the different event modules 120 relating to the newly developed events together to perform the medical scenario.

The scenario programmer 130 can, of course, write new events for incorporating into the medical training module 15. It is also possible for the scenario programmer 130 to write the newly developed events back into the event modules data base 110 where the event modules 120 can then be reused by other ones of the scenario developers 130.

Finally, in in step 330, the scenario programmer 130 provides the developed new medical training module 15 (after necessary testing) to the central administrative module 10 for implementation.

It will be understood that the system and method described herein may be performed using a general-purpose computer which is specifically programmed to perform these tasks. Additionally, the apparatus and methods described herein may be embodied as a combination of hardware and software. The software can be programmed in a variety of computer languages. To simplify the operation and the collection of data, a XML format has been developed for the medical training module 15. The individual ones of the devices on which the medical scenario is running interpret those XML instructions in an appropriate manner and can ignore those XML instructions which are not relevant to that device. It will be appreciated that the XML file format is only one example of a suitable file format. Thus, the present invention should not be limited by any of the exemplary embodiments, but should be defined only in accordance with the following claims and their equivalents.

REFERENCE NUMERALS

5 Medical Training Development System
10 Central Administrative Module
15 Medical training modules
20 Manikin
25 Data entry device
30 Personal computer
40 Data Manager
50 Students record database
60 Patient record database
70 Firewall
90 Quality control system
100 Medical Training Scenario Development System
110 Repository
120 Event modules
130 Scenario Programmer
140 Scenario programming system
150 Additional code

The invention claimed is:

1. A medical training development system for development of at least two different medical training scenarios comprising:

at least one training device adapted to run medical training scenarios;

a repository with a plurality of non-transitory memory elements for storing program code relating to at least one of a pre-programmed medical training event modules or a pre-programmed medical training scenarios, wherein both the pre-programmed medical training event modules and the pre-programmed medical scenarios comprises instructions for running on at least one training device to simulate at least one medical procedure and further comprises metadata defining descriptors; and a medical training scenario programming system connectable to the repository for accessing at least one of the pre-programmed medical training event modules or the pre-programmed medical training scenarios, for programming the medical training scenarios using the accessed one of the pre-programmed medical training event modules or the pre-programmed medical training scenarios each associated with the metadata defining descriptors, developing at least one new medical training scenario by a plurality of the pre-programmed event modules or the pre-programmed medical training scenarios each associated with the metadata defining descriptors, wherein different pre-programmed event modules or pre-programmed medical training scenarios are linked together in the scenario programming system to be performed on the at least one training device as the at least one new medical scenario and passaging of the new medical training scenario to a central administrative module;

a student record database having a plurality of records relating to experience of students; and a data entry device operative on receipt of at least one of the new medical training modules interpreting the descriptors defined by the metadata associated with the plurality of pre-programmed event modules or the pre-programmed medical training scenarios for generating instructions for entry of student performance data to the student record wherein the metadata defining descriptors are configured to enable a comparison of same ones of the pre-programmed medical training event modules in different medical training scenarios for comparing the same medical training performance data of training in different ones of the medical training scenarios performed by the same student by a medical training quality control system, wherein the metadata defining descriptors are indicative of the medical training performance of the same student performing the at least two different medical training scenarios for improving the performance of the same student.

2. The medical training development system of claim 1, further comprising groupings of medical training pre-programmed event modules in the repository.

3. The medical training development system of claim 1, wherein the pre-programmed medical training event modules are in the form of XML files.

4. The medical training development system of claim 2, wherein the pre-programmed medical training event modules are in the form of XML, files.

* * * * *